(12) United States Patent
Warner et al.

(10) Patent No.: US 11,832,824 B2
(45) Date of Patent: Dec. 5, 2023

(54) VASCULAR OCCLUSION

(71) Applicant: Terumo Corporation, Tokyo (JP)

(72) Inventors: Sheila Warner, Costa Mesa, CA (US); Jacqueline Macias, South Gate, CA (US); Jessica Liang, Irvine, CA (US); Wendy Graczyk, San Clemente, CA (US)

(73) Assignee: Terumo Corporation, Tokyo (JP)

( * ) Notice: Subject to any disclaimer, the term of this patent is extended or adjusted under 35 U.S.C. 154(b) by 1059 days.

(21) Appl. No.: 16/516,158

(22) Filed: Jul. 18, 2019

(65) Prior Publication Data

US 2019/0336132 A1 Nov. 7, 2019

Related U.S. Application Data

(63) Continuation of application No. 14/575,308, filed on Dec. 18, 2014, now Pat. No. 10,398,441.

(60) Provisional application No. 61/924,662, filed on Jan. 7, 2014, provisional application No. 61/919,667, filed on Dec. 20, 2013.

(51) Int. Cl.
*A61B 17/12* (2006.01)
*A61F 2/01* (2006.01)
*A61B 17/00* (2006.01)
*A61B 90/00* (2016.01)

(52) U.S. Cl.
CPC .... *A61B 17/12036* (2013.01); *A61B 17/1214* (2013.01); *A61B 17/12113* (2013.01); *A61B 17/12122* (2013.01); *A61B 17/12136* (2013.01); *A61B 17/12172* (2013.01); *A61F 2/0105* (2020.05); *A61B 17/1215* (2013.01); *A61B 17/12177* (2013.01);
(Continued)

(58) Field of Classification Search
CPC ........ A61B 17/12022; A61B 17/12031; A61B 17/12036; A61B 17/1204; A61B 17/12045; A61B 17/12099; A61B 17/12104; A61B 17/12109; A61B 17/12122; A61B 17/12131; A61B 17/12136; A61B 17/12168; A61B 17/12172; A61B 17/12177; A61B 17/12113; A61B 17/12118; A61B 17/0057; A61B 2017/1205; A61B 2017/00597; A61B 2017/00575; A61B 2017/00601; A61B 2017/0061; A61B 2017/00615; A61B 2017/00619; A61B 2017/00623; A61B 2017/00632; A61B 2017/00637; A61B 2017/00641
See application file for complete search history.

(56) References Cited

U.S. PATENT DOCUMENTS

| 4,364,392 A | 12/1982 | Strother et al. |
| 4,364,492 A | 12/1982 | Kong |

(Continued)

FOREIGN PATENT DOCUMENTS

| CN | 102438533 A | 5/2012 |
| EP | 1691879 B1 | 8/2006 |

(Continued)

*Primary Examiner* — Dianne Dornbusch
(74) *Attorney, Agent, or Firm* — Inskeep IP Group, Inc.

(57) ABSTRACT

An occlusive system for the vasculature and an embolic coil used in such an occlusive system is described. Also described is an occlusive plug which can be used for occlusive purposes within the vasculature.

20 Claims, 11 Drawing Sheets

(52) U.S. Cl.
CPC ............... *A61B 2017/00893* (2013.01); *A61B 2017/12054* (2013.01); *A61B 2090/3966* (2016.02)

(56) References Cited

U.S. PATENT DOCUMENTS

| | | | |
|---|---|---|---|
| 5,067,489 A | 11/1991 | Lind | |
| 5,122,136 A | 6/1992 | Guglielmi et al. | |
| 5,330,483 A | 7/1994 | Heaven et al. | |
| 5,334,210 A | 8/1994 | Gianturco | |
| 5,354,309 A | 10/1994 | Schnepp-Pesch et al. | |
| 5,397,331 A | 3/1995 | Himpens et al. | |
| 5,466,242 A | 11/1995 | Mori | |
| 5,478,331 A * | 12/1995 | Heflin .................. | A61M 25/00 604/533 |
| 5,496,277 A | 3/1996 | Termin et al. | |
| 5,499,995 A | 5/1996 | Teirstein | |
| 5,514,093 A | 5/1996 | Ellis et al. | |
| 5,662,711 A | 9/1997 | Douglas | |
| 5,713,848 A | 2/1998 | Dubrul | |
| 5,718,159 A | 2/1998 | Thompson | |
| 5,725,552 A | 3/1998 | Kotula et al. | |
| 5,741,333 A | 4/1998 | Frid | |
| 5,769,816 A * | 6/1998 | Barbut .................. | A61F 2/01 604/93.01 |
| 5,814,062 A | 9/1998 | Sepetka et al. | |
| 5,814,064 A | 9/1998 | Daniel et al. | |
| 5,846,261 A | 12/1998 | Kotula et al. | |
| 5,853,422 A | 12/1998 | Huebsch et al. | |
| 5,861,003 A | 1/1999 | Latson et al. | |
| 5,868,778 A * | 2/1999 | Gershony ............. | A61M 25/06 604/96.01 |
| 5,919,224 A | 7/1999 | Thompson et al. | |
| 5,925,060 A | 7/1999 | Forber | |
| 5,941,896 A | 8/1999 | Kerr | |
| 5,944,738 A | 8/1999 | Amplatz et al. | |
| 5,947,997 A | 9/1999 | Pavenik et al. | |
| 5,954,745 A | 9/1999 | Gertler et al. | |
| 6,010,498 A | 1/2000 | Guglielmi | |
| 6,019,786 A | 2/2000 | Thompson | |
| 6,022,336 A | 2/2000 | Zadno-Azizi et al. | |
| 6,024,754 A | 2/2000 | Engelson | |
| 6,027,520 A | 2/2000 | Tsugita et al. | |
| 6,059,814 A | 5/2000 | Ladd | |
| 6,066,149 A | 5/2000 | Samson et al. | |
| 6,113,641 A | 9/2000 | Leroy et al. | |
| 6,142,987 A | 11/2000 | Tsugita | |
| 6,152,144 A | 11/2000 | Lesh et al. | |
| 6,176,873 B1 | 1/2001 | Ouchi | |
| 6,346,117 B1 | 2/2002 | Greenhalgh | |
| 6,355,051 B1 * | 3/2002 | Sisskind ............... | A61F 2/0108 606/200 |
| 6,375,668 B1 | 4/2002 | Gifford et al. | |
| 6,379,329 B1 | 4/2002 | Nagireiter et al. | |
| 6,428,557 B1 | 8/2002 | Hilaire | |
| 6,428,558 B1 | 8/2002 | Jones et al. | |
| 6,451,048 B1 | 9/2002 | Berg et al. | |
| 6,468,303 B1 | 10/2002 | Amplatz et al. | |
| 6,550,177 B1 | 4/2003 | Epple, Jr. | |
| 6,585,748 B1 | 7/2003 | Jeffree | |
| 6,589,265 B1 | 7/2003 | Palmer et al. | |
| 6,652,555 B1 | 11/2003 | VanTassel et al. | |
| 6,685,748 B1 | 2/2004 | Day et al. | |
| 6,802,851 B2 | 10/2004 | Jones et al. | |
| 6,811,560 B2 | 11/2004 | Jones et al. | |
| 6,953,472 B2 | 10/2005 | Palmer et al. | |
| 6,994,717 B2 | 2/2006 | Kónya et al. | |
| 7,083,632 B2 | 8/2006 | Avellanet et al. | |
| 7,122,058 B2 | 10/2006 | Levine et al. | |
| 7,195,636 B2 | 3/2007 | Avellanet et al. | |
| 7,229,461 B2 | 6/2007 | Chin et al. | |
| 7,267,694 B2 | 9/2007 | Levine et al. | |
| 7,294,146 B2 | 11/2007 | Chew et al. | |
| 7,306,624 B2 | 12/2007 | Yodfat et al. | |
| 7,320,065 B2 | 1/2008 | Gosior et al. | |
| 7,326,224 B2 * | 2/2008 | Houde .................. | 606/200 |
| 7,329,285 B2 | 2/2008 | Levine et al. | |
| 7,569,066 B2 | 8/2009 | Gerberding et al. | |
| 7,632,291 B2 | 12/2009 | Stephens et al. | |
| 7,632,391 B2 | 12/2009 | Cochran | |
| 7,645,259 B2 | 1/2010 | Goldman | |
| 7,665,466 B2 | 2/2010 | Figulla et al. | |
| 7,678,129 B1 | 3/2010 | Gesswein et al. | |
| 7,691,124 B2 | 4/2010 | Balgobin | |
| 7,695,488 B2 | 4/2010 | Berenstein et al. | |
| 7,713,282 B2 | 5/2010 | Frazier et al. | |
| 7,749,238 B2 | 7/2010 | Corcoran et al. | |
| 7,762,943 B2 | 7/2010 | Khairkhahan | |
| 7,981,151 B2 | 7/2011 | Rowe | |
| 8,034,061 B2 | 10/2011 | Amplatz et al. | |
| 8,043,326 B2 | 10/2011 | Hancock et al. | |
| 8,060,183 B2 | 11/2011 | Leopold et al. | |
| 8,062,251 B2 | 11/2011 | Goldman | |
| 8,066,732 B2 | 11/2011 | Paul et al. | |
| 8,083,792 B2 | 12/2011 | Boucher et al. | |
| 8,142,456 B2 | 3/2012 | Rosqueta et al. | |
| 8,152,833 B2 | 4/2012 | Zaver et al. | |
| 8,251,948 B2 | 8/2012 | Goldman | |
| 8,262,719 B2 | 9/2012 | Erickson et al. | |
| 8,280,486 B2 | 10/2012 | Miller et al. | |
| 8,308,752 B2 | 11/2012 | Tekulve | |
| 8,313,505 B2 | 11/2012 | Amplatz et al. | |
| 8,352,014 B2 | 1/2013 | Leipold et al. | |
| 8,357,180 B2 | 1/2013 | Feller, III et al. | |
| 8,361,111 B2 | 1/2013 | Widomski et al. | |
| 8,361,138 B2 | 1/2013 | Adams | |
| 8,398,670 B2 | 3/2013 | Amplatz et al. | |
| 8,408,212 B2 | 4/2013 | O'Brien et al. | |
| 8,425,548 B2 | 4/2013 | Connor | |
| 8,433,391 B2 | 4/2013 | Mark | |
| 8,442,623 B2 | 5/2013 | Nicoson et al. | |
| 8,454,633 B2 | 6/2013 | Amplatz et al. | |
| 8,460,366 B2 | 6/2013 | Rowe | |
| 8,480,702 B2 | 7/2013 | Kusleika et al. | |
| 8,491,612 B2 | 7/2013 | Stopek et al. | |
| 8,523,940 B2 | 9/2013 | Richardson et al. | |
| 8,636,760 B2 | 1/2014 | Garcia et al. | |
| 8,663,301 B2 | 3/2014 | Riina et al. | |
| 8,671,815 B2 | 3/2014 | Hancock et al. | |
| 8,679,150 B1 | 3/2014 | Janardhan et al. | |
| 8,685,055 B2 | 4/2014 | VanTassel et al. | |
| 8,690,907 B1 | 4/2014 | Janardhan et al. | |
| 8,696,701 B2 | 4/2014 | Becking et al. | |
| 8,715,314 B1 | 5/2014 | Janardhan et al. | |
| 8,715,315 B1 | 5/2014 | Janardhan et al. | |
| 8,715,316 B1 | 5/2014 | Janardhan et al. | |
| 8,715,317 B1 | 5/2014 | Janardhan et al. | |
| 8,715,338 B2 | 5/2014 | Frid | |
| 8,721,676 B1 | 5/2014 | Janardhan et al. | |
| 8,721,677 B1 | 5/2014 | Janardhan et al. | |
| 8,721,707 B2 | 5/2014 | Boucher et al. | |
| 8,728,112 B2 | 5/2014 | Evert et al. | |
| 8,728,116 B1 | 5/2014 | Janardhan et al. | |
| 8,728,117 B1 | 5/2014 | Janardhan et al. | |
| 8,728,141 B2 | 5/2014 | Riina et al. | |
| 8,733,618 B1 | 5/2014 | Janardhan et al. | |
| 8,734,483 B2 | 5/2014 | Tekulve et al. | |
| 8,735,777 B1 | 5/2014 | Janardhan et al. | |
| 8,747,432 B1 | 6/2014 | Janardhan et al. | |
| 8,747,453 B2 | 6/2014 | Amplatz et al. | |
| 8,747,462 B2 | 6/2014 | Hill et al. | |
| 8,747,597 B2 | 6/2014 | Rosqueta et al. | |
| 8,753,371 B1 | 6/2014 | Janardhan et al. | |
| 8,758,426 B2 | 6/2014 | Hood et al. | |
| 8,764,772 B2 | 7/2014 | Tekulve | |
| 8,764,787 B2 | 7/2014 | Ren | |
| 8,777,974 B2 | 7/2014 | Amplatz et al. | |
| 8,777,979 B2 | 7/2014 | Shrivastava et al. | |
| 8,778,008 B2 | 7/2014 | Amplatz et al. | |
| 8,783,151 B1 | 7/2014 | Janardhan et al. | |
| 8,784,446 B1 | 7/2014 | Janardhan et al. | |
| 8,789,452 B1 | 7/2014 | Janardhan et al. | |
| 8,790,365 B1 | 7/2014 | Janardhan et al. | |
| 8,795,316 B2 | 8/2014 | Balgobin et al. | |

(56) References Cited

U.S. PATENT DOCUMENTS

| | | |
|---|---|---|
| 8,795,319 B2 | 8/2014 | Ryan et al. |
| 8,795,330 B1 | 8/2014 | Janardhan et al. |
| 8,803,030 B1 | 8/2014 | Janardhan et al. |
| 8,813,625 B1 | 8/2014 | Janardhan et al. |
| 8,816,247 B1 | 8/2014 | Janardhan et al. |
| 8,821,529 B2 | 9/2014 | Kariniemi et al. |
| 8,821,849 B2 | 9/2014 | Schwartz |
| 8,828,043 B2 | 9/2014 | Chambers |
| 8,828,045 B1 | 9/2014 | Janardhan et al. |
| 8,828,051 B2 | 9/2014 | Javois et al. |
| 8,845,678 B1 | 9/2014 | Janardhan et al. |
| 8,845,679 B1 | 9/2014 | Janardhan et al. |
| 8,852,227 B1 | 10/2014 | Janardhan et al. |
| 8,859,934 B1 | 10/2014 | Janardhan et al. |
| 8,863,631 B1 | 10/2014 | Janardhan et al. |
| 8,866,049 B1 | 10/2014 | Janardhan et al. |
| 8,869,670 B1 | 10/2014 | Janardhan et al. |
| 8,870,901 B1 | 10/2014 | Janardhan et al. |
| 8,870,910 B1 | 10/2014 | Janardhan et al. |
| 8,872,068 B1 | 10/2014 | Janardhan et al. |
| 8,876,849 B2 | 11/2014 | Kratzberg et al. |
| 8,882,787 B2 | 11/2014 | Brenzel et al. |
| 8,882,797 B2 | 11/2014 | Janardhan et al. |
| 8,895,891 B2 | 11/2014 | Janardhan et al. |
| 8,900,287 B2 | 12/2014 | Amplatz et al. |
| 8,904,914 B2 | 12/2014 | Janardhan et al. |
| 8,905,961 B2 | 12/2014 | Braido et al. |
| 8,906,057 B2 | 12/2014 | Connor et al. |
| 8,910,555 B2 | 12/2014 | Janardhan et al. |
| 8,945,170 B2 | 2/2015 | Paul, Jr. |
| 9,011,476 B2 | 4/2015 | Sideris |
| 9,295,571 B2 | 3/2016 | Newell et al. |
| 9,579,104 B2 | 2/2017 | Beckham et al. |
| 9,770,234 B2 | 9/2017 | Sideris et al. |
| 10,398,441 B2 | 9/2019 | Warner et al. |
| 10,405,866 B2 | 9/2019 | Chakraborty et al. |
| 10,952,740 B2 | 3/2021 | Dasnurkar et al. |
| 2001/0000797 A1 | 5/2001 | Mazzochi |
| 2001/0012949 A1 | 8/2001 | Forber |
| 2002/0042628 A1 | 4/2002 | Chin et al. |
| 2002/0082638 A1 | 6/2002 | Porter et al. |
| 2002/0111647 A1 | 8/2002 | Khairkhahan et al. |
| 2002/0123759 A1 | 9/2002 | Amplatz |
| 2002/0143349 A1 | 10/2002 | Gifford, III et al. |
| 2002/0156499 A1 | 10/2002 | Konya et al. |
| 2002/0165572 A1 | 11/2002 | Saadat |
| 2002/0189727 A1 | 12/2002 | Peterson |
| 2003/0023299 A1 | 1/2003 | Amplatz et al. |
| 2003/0199919 A1 | 6/2003 | Palmer et al. |
| 2003/0167068 A1 | 9/2003 | Amplatz |
| 2003/0220666 A1 | 11/2003 | Mirigian et al. |
| 2004/0044361 A1 | 3/2004 | Frazier et al. |
| 2004/0049210 A1 | 3/2004 | VanTassel et al. |
| 2004/0193206 A1* | 9/2004 | Gerberding ...... A61B 17/12022 606/200 |
| 2005/0065484 A1 | 3/2005 | Watson, Jr. |
| 2005/0070952 A1 | 3/2005 | Devellian |
| 2005/0228434 A1 | 10/2005 | Amplatz et al. |
| 2005/0234543 A1 | 10/2005 | Glaser et al. |
| 2005/0288706 A1 | 12/2005 | Widomski et al. |
| 2006/0161110 A1* | 7/2006 | Lenker ............. A61B 17/00491 604/183 |
| 2006/0206139 A1 | 9/2006 | Tekulve |
| 2006/0206193 A1 | 9/2006 | Chobotov et al. |
| 2006/0241690 A1 | 10/2006 | Amplatz et al. |
| 2006/0247680 A1 | 11/2006 | Amplatz et al. |
| 2007/0055302 A1 | 3/2007 | Henry et al. |
| 2007/0066993 A1 | 3/2007 | Kreidler |
| 2007/0112380 A1 | 5/2007 | Figulla et al. |
| 2007/0135826 A1 | 6/2007 | Zaver et al. |
| 2007/0167980 A1 | 7/2007 | Figulla et al. |
| 2007/0179520 A1 | 8/2007 | West |
| 2007/0233186 A1 | 10/2007 | Meng |
| 2007/0239192 A1 | 10/2007 | Litzenberg et al. |
| 2007/0270891 A1 | 11/2007 | McGuckin, Jr. |
| 2008/0033480 A1 | 2/2008 | Hardert |
| 2008/0097495 A1 | 4/2008 | Feller, III et al. |
| 2008/0103585 A1 | 5/2008 | Monstadt et al. |
| 2008/0119887 A1 | 5/2008 | Que et al. |
| 2008/0249562 A1 | 10/2008 | Cahill |
| 2008/0262518 A1 | 10/2008 | Freudenthal |
| 2008/0281350 A1 | 11/2008 | Sepetka et al. |
| 2008/0306504 A1 | 12/2008 | Win et al. |
| 2009/0018562 A1 | 1/2009 | Amplatz et al. |
| 2009/0062845 A1 | 3/2009 | Tekulve |
| 2009/0082803 A1 | 3/2009 | Adams et al. |
| 2009/0187214 A1 | 7/2009 | Amplatz et al. |
| 2009/0209855 A1 | 8/2009 | Drilling et al. |
| 2009/0216263 A1 | 8/2009 | Tekulve |
| 2010/0010517 A1 | 1/2010 | Stopek et al. |
| 2010/0030200 A1 | 2/2010 | Strauss et al. |
| 2010/0106235 A1 | 4/2010 | Kariniemi et al. |
| 2010/0160847 A1 | 6/2010 | Braido et al. |
| 2010/0318097 A1 | 12/2010 | Ferrera et al. |
| 2010/0324586 A1 | 12/2010 | Miles et al. |
| 2011/0040324 A1 | 2/2011 | McCarthy et al. |
| 2011/0046719 A1 | 2/2011 | Frid |
| 2011/0082491 A1 | 4/2011 | Sepetka et al. |
| 2011/0118776 A1 | 5/2011 | Chen et al. |
| 2011/0265943 A1 | 11/2011 | Rosqueta et al. |
| 2011/0276080 A1 | 11/2011 | Nigon |
| 2011/0295298 A1 | 12/2011 | Moszner |
| 2011/0301630 A1 | 12/2011 | Hendriksen et al. |
| 2012/0041472 A1 | 2/2012 | Tan et al. |
| 2012/0046683 A1 | 2/2012 | Wilson et al. |
| 2012/0143008 A1 | 6/2012 | Wilkins et al. |
| 2012/0172928 A1 | 7/2012 | Eidenschink et al. |
| 2012/0215152 A1 | 8/2012 | Levine et al. |
| 2012/0239066 A1* | 9/2012 | Levine ........... A61B 17/320758 606/159 |
| 2012/0245668 A1 | 9/2012 | Kariniemi et al. |
| 2012/0330341 A1 | 12/2012 | Becking et al. |
| 2012/0330348 A1 | 12/2012 | Strauss et al. |
| 2013/0012979 A1 | 1/2013 | Amplatz et al. |
| 2013/0018413 A1 | 1/2013 | Oral et al. |
| 2013/0085521 A1 | 4/2013 | Lim |
| 2013/0138136 A1 | 5/2013 | Beckham et al. |
| 2013/0190798 A1 | 7/2013 | Kapadia |
| 2013/0211443 A1 | 8/2013 | Cragg et al. |
| 2013/0245667 A1 | 9/2013 | Marchand et al. |
| 2013/0274868 A1 | 10/2013 | Cox et al. |
| 2014/0172001 A1 | 6/2014 | Becking et al. |
| 2014/0172004 A1 | 6/2014 | De Canniere |
| 2014/0222132 A1 | 8/2014 | Boucher et al. |
| 2016/0192912 A1 | 7/2016 | Kassab et al. |
| 2017/0042549 A1 | 2/2017 | Kaplan et al. |
| 2018/0338767 A1 | 11/2018 | Dasnurkar et al. |
| 2021/0330333 A1 | 10/2021 | Gray et al. |

FOREIGN PATENT DOCUMENTS

| | | |
|---|---|---|
| EP | 1994887 A1 | 11/2008 |
| JP | 2003-529410 A | 10/2003 |
| JP | 2007-519498 A | 7/2007 |
| JP | 2008536620 A | 9/2008 |
| JP | 2012523943 A | 10/2012 |
| WO | WO2000/072909 A1 | 12/2000 |
| WO | WO 2001/030266 A1 | 5/2001 |
| WO | WO2014/146001 A2 | 9/2004 |
| WO | WO 2005/074814 A2 | 8/2005 |
| WO | WO 2005/074814 A3 | 8/2005 |
| WO | WO2006/115689 A1 | 11/2006 |
| WO | WO2010/123821 A1 | 10/2010 |
| WO | WO2013/005195 A1 | 1/2013 |
| WO | WO 2013/068466 A1 | 5/2013 |
| WO | WO2014/144980 A1 | 9/2014 |
| WO | WO2014/145005 A2 | 9/2014 |

* cited by examiner

VASCULAR OCCLUSION

RELATED APPLICATIONS

This application is a continuation of U.S. patent application Ser. No. 14/575,308 filed Dec. 18, 2014 entitled Vascular Occlusion, now issued as U.S. Pat. No. 10,398,441, which claims benefit of and priority to U.S. Provisional Application Ser. No. 61/919,667 filed Dec. 20, 2013 entitled Vascular Occlusion, and U.S. Provisional Application Ser. No. 61/924,662 filed Jan. 7, 2014 entitled Vascular Plug, all of which are hereby incorporated herein by reference in their entireties.

BACKGROUND OF THE INVENTION

Occlusion is often used as a treatment for various vascular disorders, such as aneurysm, atrial septal defect, left atrial appendage, patent foramen ovale, patent ductus arteriosis, and the like. The use of embolic coils is one method of occlusion. However, on occasion there are difficulties that can arise. For example, occlusion within the left atrial appendage can be particularly difficult because of the potential variance in the shape of the ostium of the left atrial appendage, and the potential variance in the shape and geometry of the left atrial appendage. Also, one possible complication with embolic coils is the risk of the coils falling out of the target treatment site within the vasculature. Accordingly, a system of occlusion utilizing embolic coils which mitigates the risk of the coils falling out of the target treatment site would be beneficial. Also beneficial would be devices and methods which improve the occluding process in general. Such a system would be widely useful for treating various disorders, including the occlusion of left atrial appendages, aneurysms, atrial septal defect, patent foramen ovale, patent ductus arteriosis, vessel shutdown and other similar vascular disorders.

SUMMARY OF THE INVENTION

In one embodiment an occlusive system comprises a containment bag and embolic coils.

In one embodiment an occlusive system comprises a containment bag, balloon, and embolic coils.

In another embodiment an embolic coil used in an occlusive system is described.

In another embodiment an occlusive system comprises a protective disk and embolic coils.

In another embodiment an occlusive system comprises a protective mesh, and embolic coils.

In another embodiment an occlusive system comprises a balloon and embolic coils.

In another embodiment an occlusive system includes an embolic coil having a sheet.

In another embodiment an embolic coil used in an occlusive system includes a sheet.

In another embodiment an occluder with an inner structure and outer structure is described.

In another embodiment an occluder with an inner structure and outer membrane layer is described.

In another embodiment an occluder with an inner and outer structure and intermediate membrane layer is described.

In another embodiment an occluder is collapsible.

In another embodiment an occluder is not collapsible.

These and other objects and features of the present invention will be appreciated upon consideration of the following drawings and detailed descriptions.

DESCRIPTION OF EMBODIMENTS

I. Vascular Occlusion System

An occlusive system is used to occlude a vascular treatment site. In some of the examples specified, the occlusive system is used to treat the left atrial appendage, although the system could also be used for other purposes such as aneurysm occlusion or other occlusive purposes. The left atrial appendage is a pouch located in the left atrium. In some cases blood clots may form in the appendage. Over time thrombus from the clots may dislodge and lead to thrombus formation in other areas of the vasculature, leading to ischemic damage such as stroke. Thus occlusion of the left atrial appendage tends to limit and sometimes prevent this thrombus migration.

The embodiments described may be used to occlude left atrial appendages, atrial septal defects, patent foramen ovale, aneurysms, and other vascular disorders.

Figure 1:
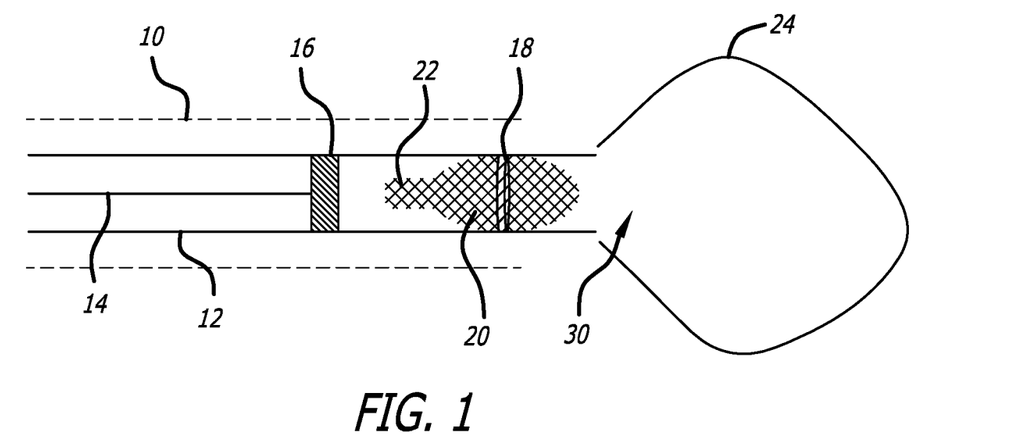
FIGS. 1-5 are plan renderings of an occlusive system of one embodiment used to treat a vascular defect in accordance with the present invention.

FIG. 1 shows an occlusive system. The system is deployed within the vasculature and placed in the vicinity of the left atrial appendage (LAA) 24. The system is deployed through a catheter 10 and includes a delivery tube 12. In one example the system is delivered through a guide catheter 10, in another example catheter 10 is a microcatheter which tube 12 is delivered through. A containment bag 20 sits near the distal end of the delivery tube. The containment bag includes a proximal stem section 22. In one example the containment bag 20 is a mesh comprising one or more metallic (i.e. nitinol, stainless steel, or cobalt-chromium) filaments. The mesh may also contain one or more radiopaque threads (i.e. platinum, palladium, or tantalum) woven through the mesh to increase radiopacity and visualization.

The delivery tube 12 has a stopper ring 18 near the distal end of the delivery tube 12; the stopper ring 18 is affixed to the inner surface of the delivery tube 12. A pusher 14 with a plunger 16 at the distal end of the pusher 14 is used to push the containment bag 20. The containment bag 20 is not constrained by the stopper ring 18. In one example the containment bag 20 is made of a highly conformable mesh to thus be able to adopt a flexible shape to navigate around the stopper ring 18. In another example the containment bag 20 has a tapered profile, or does not fill the delivery tube 12 and thus the stopper ring 18 does not limit the movement of the containment bag. The pusher 14 may be comprised of a metallic material (i.e. stainless steel, nitinol, cobalt-chromium or other materials) and has a larger diameter plunger 16 attached to the distal end of the pusher 14.

The delivery tube 12 is placed in the region of the ostium (neck or opening) 30 of the left atrial appendage 24. The delivery tube may be placed just proximal of the ostium, even with the ostium, or within the left atrial appendage. The user pushes pusher 14 in order to push the containment bag 20 into the LAA 24. The plunger 16 is prohibited from moving beyond a certain point by interacting with stopper ring 18. Once the pusher 14 is pushed to a certain point the plunger 16 hits the stopper ring 18 which limits any further movement. The plunger 16 pushes against the stem 22 of containment bag 20. Due to the force from the plunger 16, the containment bag 20 pushes into the LAA where the proximal part of the bag sits near the ostium while the distal portion sits within the LAA. Depending on the size of the cavity, the containment bag 20 may fill a substantial portion of the LAA, or sit mostly within the ostium. The intended function of containment bag 20 is to act as a filling receptacle for subsequently placed embolic coils, to prevent blood flow into and out of the target site.

Figure 2:
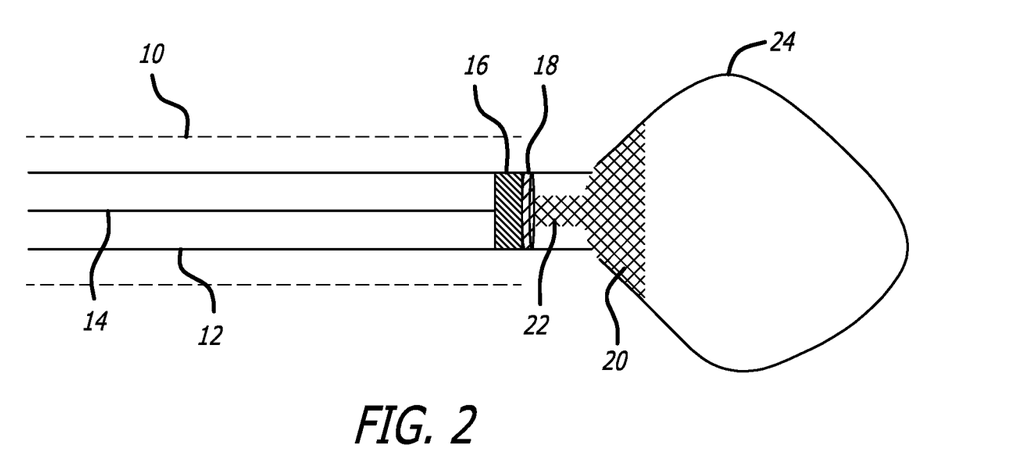
Figure 3:
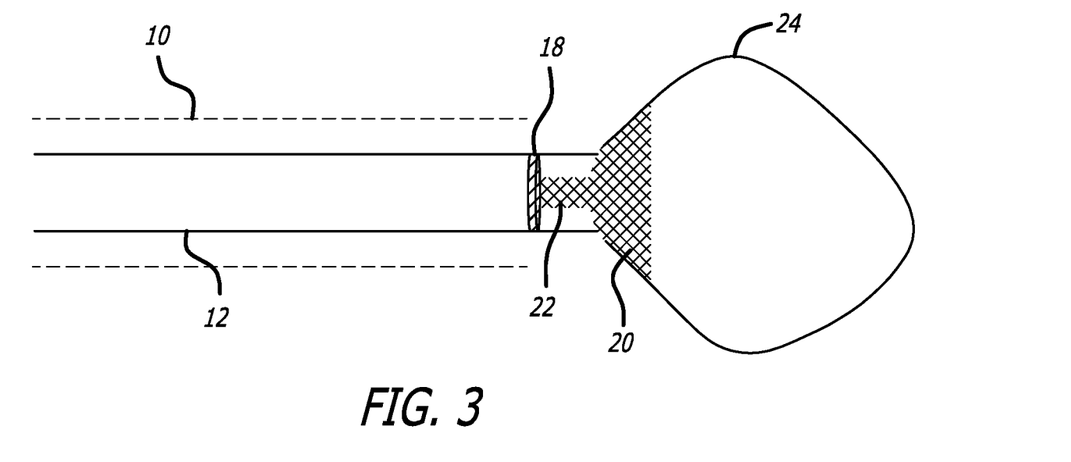
Figure 4:
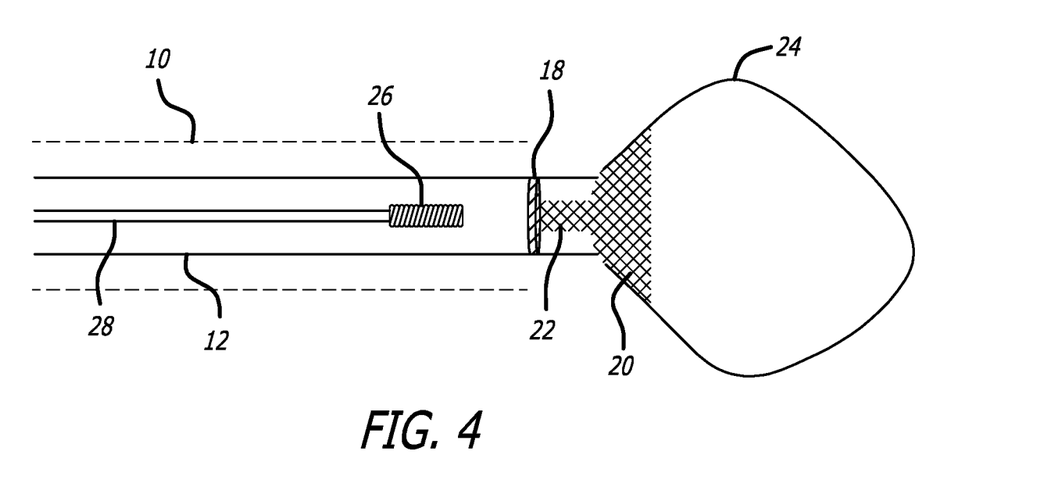
Figure 5:
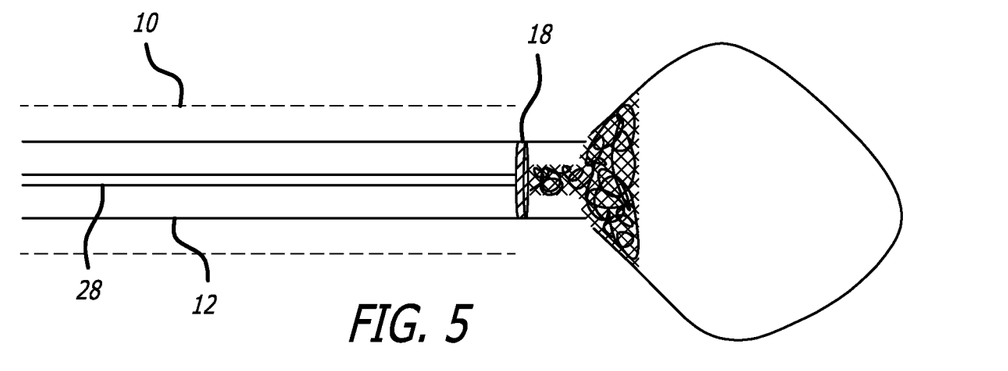

In FIG. 2, pusher 14 is pushed to the point where plunger 16 hits stopper ring 18. Containment bag 20 is pushed into the LAA, and pusher 14 is withdrawn (FIG. 3). Referring to FIG. 4, another pusher 28 with distally attached embolic coil 26 is placed through tube 12. The embolic coil 26 is pushed into the containment bag 20. Thermal, electrolytic, or mechanical detachment means can be used to detach the coil 26 from the pusher 28. One such thermal detachment system that could be used is shown in U.S. Pat. No. 8,182,506, which is hereby incorporated by reference in its entirety. Another detachment system that could be used is shown in U.S. Pat. No. 6,620,152, which is hereby incorporated by reference in its entirety. With reference to FIG. 5, this procedure can be repeated to fill the bag with additional embolic coils 26. The coils 26 are retained within the containment bag 20 and the coils 26 form a solid embolic mass within the bag and fill the space at the neck of the malformation to prevent blood flow into the malformation.

Various types of embolic coils can be used to fill the containment bag. Examples include those described in U.S. Pat. Nos. 8,273,100, 8,066,036, 6,375,669, 6,015,424, 8,323,306, 8,377,091, and U.S. Pub. No. 2011/184455 all of which are hereby incorporated by reference in their entirety. The embolic coils can utilize polymers, hydrogels, and/or metals such as platinum, nitinol, stainless steel.

Another embodiment would incorporate a compliant balloon (not shown) with the containment bag occlusive system. In one example, the compliant balloon (not shown) would come pre-loaded in the distal portion of the containment bag 20 and thereby provide a buffer against which the coils would rest at the distal end of the containment bag 20. The balloon would be preloaded in the containment bag 20.

In another example, a balloon catheter would be situated so that the catheter balloon is placed at the neck of the malformation so that the coils do not fall out of the containment bag 20. Once the bag 20 is filed, the balloon would be detached from the catheter. In other words, the compliant balloon would be introduced after the embolic coiling procedure in order to seal the neck of the malformation and provide a proximal barrier for the embolic coils to prevent migration.

Although the embodiment as described above is shown for use for occluding a left atrial appendage, it could also be used for a variety of purposes including aneurysm, atrial septal defect, patent foramen ovale, or other occlusive purposes.

Another embodiment in accordance with the present invention is shown in FIGS. 6-12. An occlusive system comprises a tubular assembly 31 that has an inner tube 40 which is disposed within an outer tube 38. The outer tube 38 has a lumen to accommodate the inner tube 40, and the inner tube 40 also has a lumen.

Figure 6:
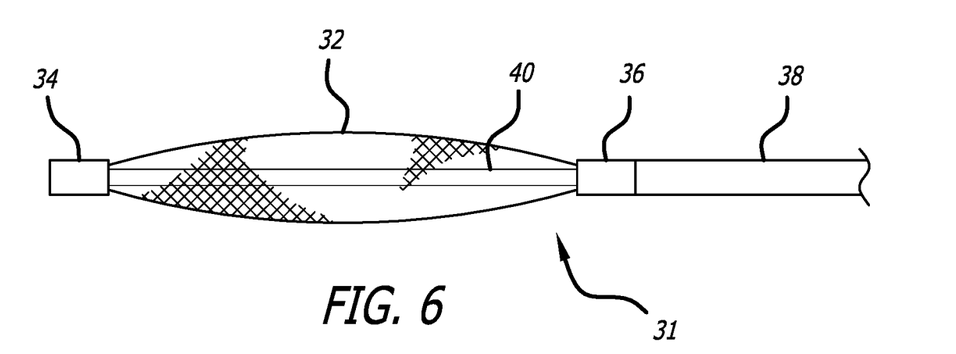
FIGS. 6-12 are plan renderings of an occlusive system of another embodiment in accordance with the present invention.
Figure 7:
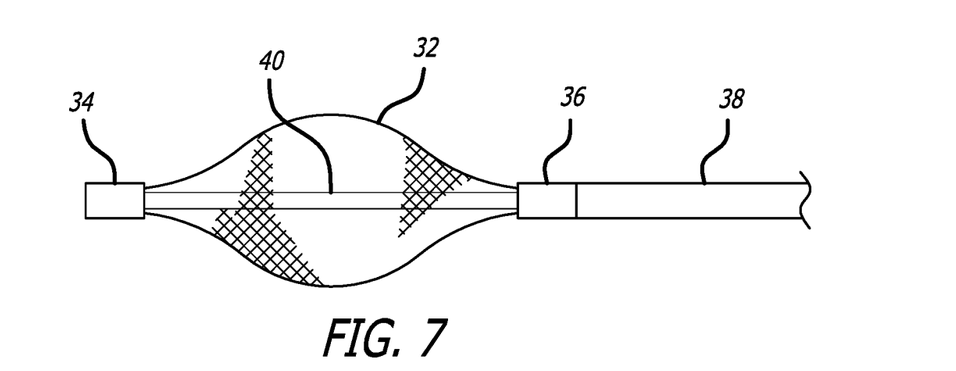
Figure 8:
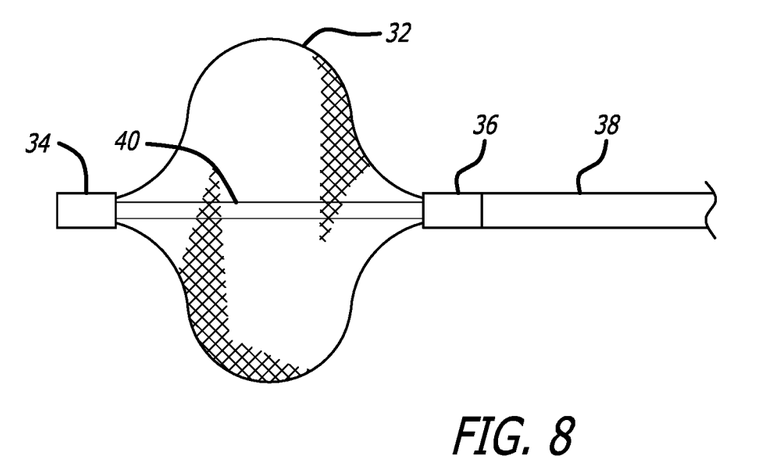
Figure 9:
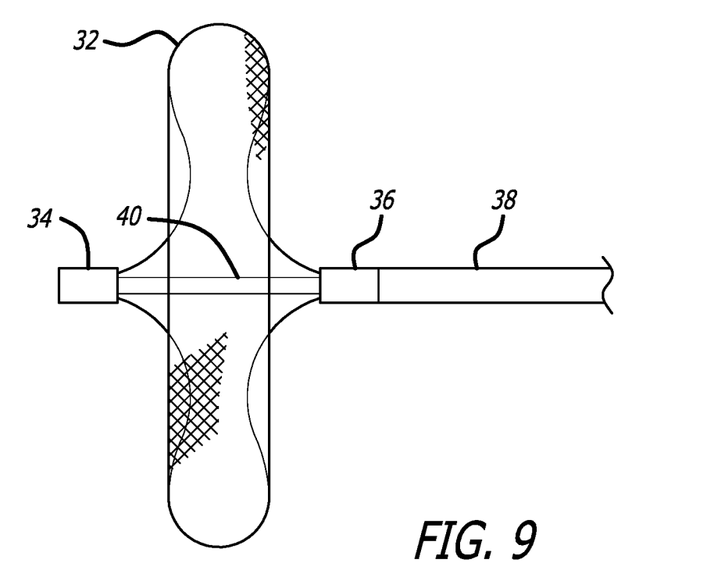
Figure 10:
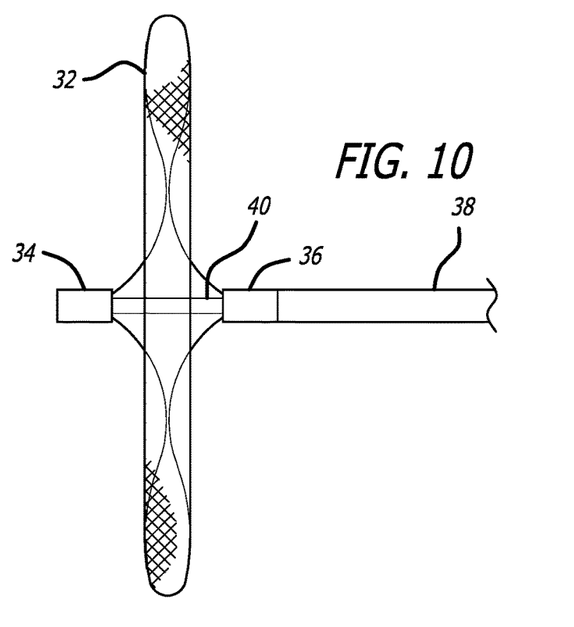

A mesh structure 32 is disposed at the distal end of the tubular assembly 31 and is affixed to the distal end of the inner tube 40 at location 34 and to the distal end of the outer tube 38 at location 36. Such affixation can be made through various techniques known to those skilled in the art, including mechanical ties, chemical affixation, over-molding or various combinations thereof. The mesh structure 32 can be comprised of a mesh of nitinol, cobalt chromium, or other metallic wires. Radiopaque material (i.e. tantalum or platinum) may optionally be used in the mesh to enhance visualization.

The mesh structure 32 will generally have an elongated shape but will adopt a disk-like, bunched shape based on user manipulation of the tubular assembly 31, as will be explained in more detail below.

The inner tube 40 is movable relative to the outer tube 38. Since one end of the mesh structure 31 is attached to the outer tube 38 and its opposite end is attached to the inner tube 40, movement of inner tube 40 relative to the outer tube 38 will selectively cause the mesh structure 32 to adopt the shapes shown in FIGS. 7-10 as the inner tube is retracted.

For example, as the inner tube 40 is retracted relative to the outer tube 38, the mesh structure 32 will adopt a more bulged, disk-like shape. Such a shape can be useful for sealing the neck of the ostium of a treatment site (e.g., the ostium of a left atrial appendage). Once the mesh structure 32 is configured to a desired shape, e.g., a sealing shape, the inner tube 40 can be used to deliver embolic agents such as embolic coils to fill the treatment site, e.g., to fill a malformation.

Figure 11:
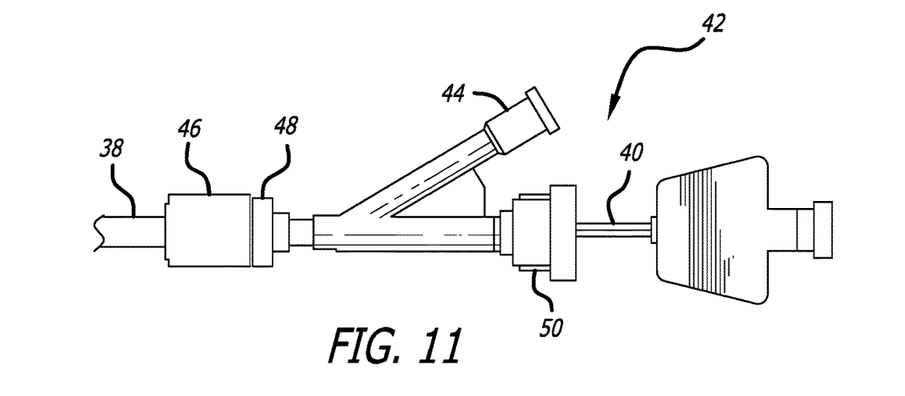
Figure 12:
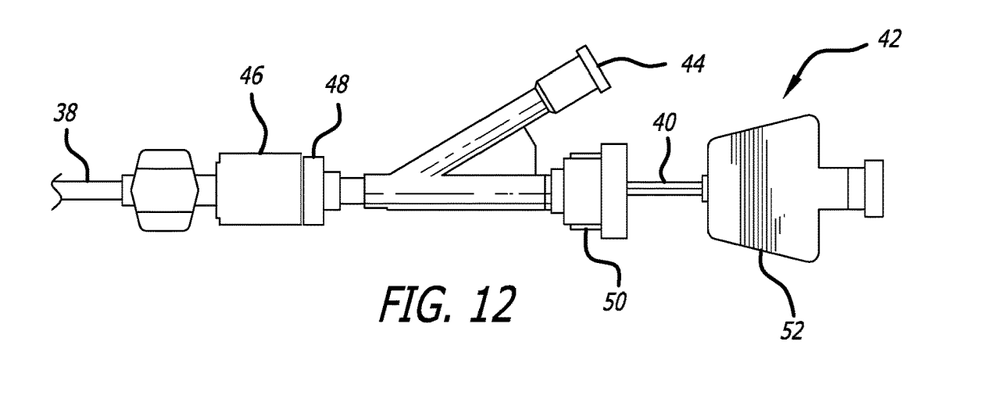

Referring now to FIGS. 11-12, the proximal portion of the tubular assembly 31 is shown. The proximal portion includes a hemostatic valve 42 which is connected to a first fitting 46, which, in turn, is connected to outer tube 38. The first fitting 46 threadably engages a second fitting 48 of the hemostatic valve 42 in a male-female relationship. Hemostatic valve 42 includes a port 44. The hemostaticvalve 42 threadably engages with third fitting 50 in a male-female relationship. Through the channel of the hemostatic valve 42 and the third fitting 50, the inner tube 40 of the tubular assembly 31 extends.

When third fitting 50 is completely threaded over the hemostatic valve 42, the third I fitting 50 clamps down on the inner tube 40 and fixes it in place relative to the outer tube 38. In other words, the third fitting 50 can be used to lock the inner tube 40 in a position relative to the outer tube 38 and thereby fix the shape of mesh structure 32.

In one example, the inner tube 40 is retracted relative to the outer tube 38 to create an optimal ostium sealing shape for mesh structure 32. The third fitting 50 is then locked to maintain the sealing shape of the mesh structure 32 while embolic agents such as coils are delivered through the inner tube 40 to the vascular treatment site.

The proximal end of the inner tube 40 has an introducer section 52. Coils can be introduced through this section, or section 52 can be connected to a syringe or other device to introduce other embolic agents (i.e. liquid embolic) into the treatment site through the inner tube 40.

In this embodiment, inner tube 40 acts like a microcatheter since it can be used to introduce embolic material and outer tube 38 acts like a sheath for the inner tube 40.

A device in accordance with the present invention may be delivered through a guide catheter to a target treatment site. The guide catheter can be retracted or the mesh structure 32 can be pushed out from the guide catheter to expose the mesh structure 32. Once the device reaches the treatment site the user can manipulate the shape of the mesh structure 32 to seal the ostium or neck of the treatment site. Once the ostium is sealed the user can implant embolic agents via the inner tube 40 to fill the vasculature, while the mesh structure 32 will prevent the embolic agent from migrating. The embolic agents, in one example coils, will form an embolic mass to seal the interior of the malformation and thus prevent blood flow into the malformation/treatment site. The mesh structure 32 can then be retracted (via relative movement of inner tube 40 and outer tube 38) to its elongated shape and withdrawn.

In one example, the system of FIGS. 6-12 has a working length of 117 cm and an overall length of 135 cm and is compatible with a 0.018" or 0.035" embolic coil. The mesh structure 32 may have a compressed length of 0.7 cm and stretched length of 2.5 cm. Outer tube 38 can have an inner diameter of 0.079" and outer diameter of 0.092" while inner tube 40 can have an inner diameter of 0.053" and outer diameter of 0.066". In one example the mesh structure 32 has a fully stretched radius of 10 mm and a fully compressed radius of 35 mm, and thus could seal an ostium having a width of 10-35 mm. In one example, the system is delivered through an 8 or 8.5 F guide catheter.

Although the embodiment as just described is shown for occluding a left atrial appendage, it could also be used for a variety of purposes including aneurysm, atrial septal defect, patent foramen ovale, or other occlusive purposes.

Figure 13:
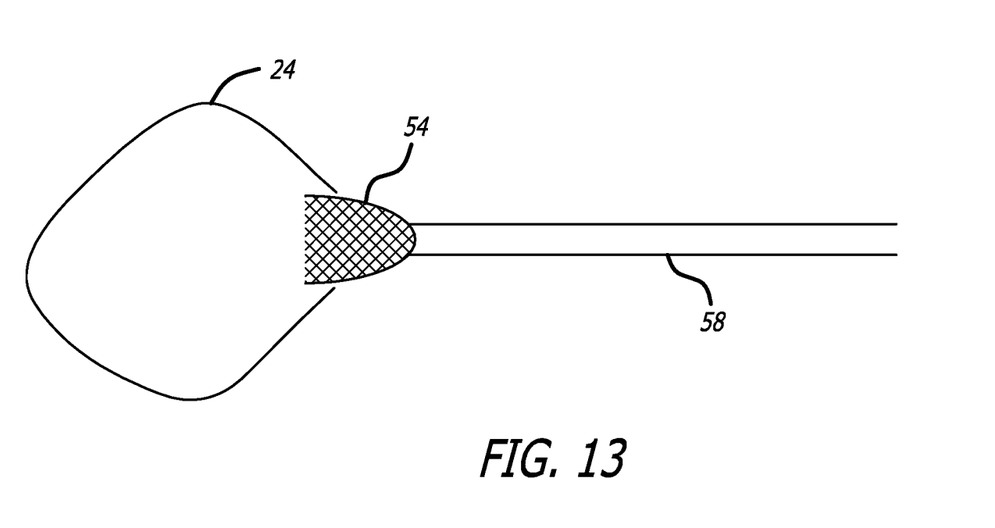
FIG. 13 is a plan rendering of an occlusive system of another embodiment in accordance with the present invention.

FIG. 13 shows another embodiment of an occlusive system. In this embodiment a mesh 54 is placed at the distal end of tube 58. The mesh 54 can be comprised of a mesh of nitinol, cobalt chromium, or other metallic wires. Radiopaque material (i.e. tantalum or platinum) may optionally be used in the mesh 54 to enhance visualization.

Tube 58 is analogous to outer tube 38 of the previous embodiment; however, no inner tube is used in this embodiment. The proximal end of mesh 54 is affixed to the distal end of tube 58, and the distal end of mesh 54 is open. Mechanical ties, chemical affixation, over molding, or various combinations thereof may be used to affix the mesh to the distal part of tube 58. The mesh naturally has a flared shape useful for sealing the neck of the ostium or neck of the treatment site. An introducer, such as a hemostatic valve or other introducer system, is disposed at the proximal end of tube 58 and is used to introduce embolic coils or other embolic agents through tube 58.

In this embodiment, tube 58 acts like a microcatheter since it can be used to introduce embolic material.

The device may be delivered through a guide catheter to a target treatment site 24. Once at the treatment site the guide catheter is retracted or the mesh 54 is pushed out from the guide catheter. The open face of the mesh is placed just distal of the neck to seal the neck for the embolic agents that are subsequently introduced. Embolic agents, such as coils, are introduced through tube 58 and the mesh seals the neck of the treatment site in order to prevent the coils from falling out. The embolic agents will form an embolic mass within the treatment site and thereby cut off blood flow to said aneurysm, left atrial appendage, or vascular malformation. The mesh 54 can then be withdrawn.

In one example, the system of FIG. 13 has an overall length of 120 cm, a working length of 50 cm and the mesh 54 has a diameter of 10 millimeters and a stretched (i.e. when compressed in a delivery catheter) length of 3 cm and an unstretched (i.e. when in an unfurled deployed state) length of 1.5 cm. In one example, the system is delivered through an 8 or 8.5 F guide catheter.

Although the embodiment as just described is shown for occluding a left atrial appendage, it could also be used for a variety of purposes including aneurysm, atrial septal defect, patent foramen ovale, or other occlusive purposes.

Figure 14:
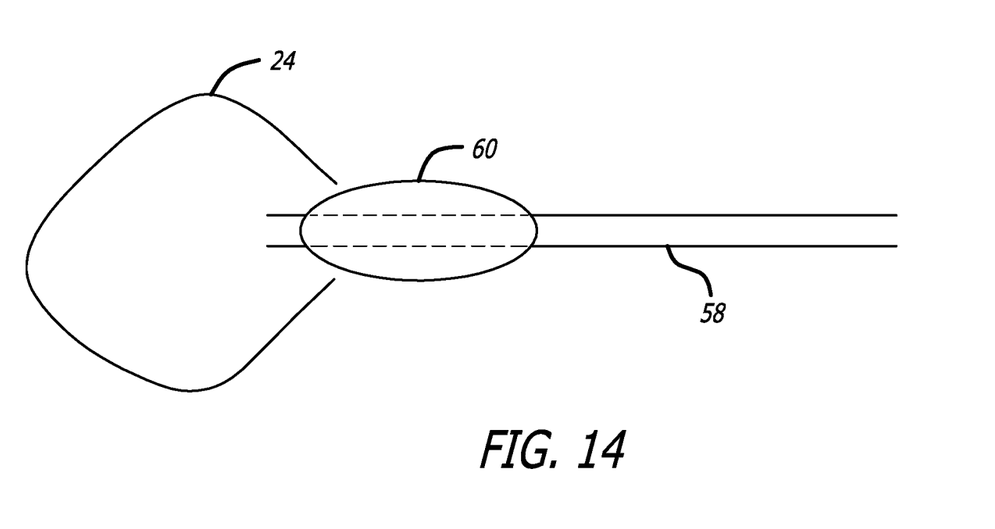
FIG. 14 is a plan rendering an occlusive system of yet another embodiment in accordance with the present invention.

In another embodiment shown in FIG. 14, the occlusive system utilizes an inflatable balloon 60 to seal the ostium. The occlusive system also utilizes a tube (e.g. microcatheter) 62 which sits proximal of the balloon and runs through the balloon. The tube 62 may incorporate an inflation lumen, or a separate inflation lumen can be used to inflate and deflate the balloon 60. The tube is used to introduce embolic agents (i.e. embolic coils).

The system is placed just distal of the treatment site and the balloon 60 is expanded at the neck or ostium 24. Embolic agents (i.e. coils) are then introduced through the tube into the malformation and the inflated balloon ensures the coils will not fall out. The embolic coils, if used, will be formed into an embolic mass, the balloon 60 can then be deflated and removed and the embolic mass will stay within the ostium to prevent blood flow into the malformation. Any polymer can be used on the balloon, such as PTFE.

In one example, tube 62 has an inner diameter of 0.072" and an outer diameter of 0.092" and the system has a working length of 101 cm and an overall length of 114 cm.

Though the embodiment as just described is shown for use for occluding a left atrial appendage, it could also be used for a variety of purposes including aneurysm, atrial septal defect, patent foramen ovale, or other occlusive purposes.

Various types of embolic coils can be used to fill the malformation, utilizing the occlusive systems described. Examples include those described in U.S. Pat. Nos. 8,273,100, 8,066,036, 6,375,669, 6,015,424, 8,323,306, 8,377,091 and U.S. Publication No. 2011/184455, all of which are hereby incorporated by reference in their entirety. The embolic coils can utilize polymers, hydrogels, and/or metals such as platinum, nitinol, stainless steel.

The coils will typically be delivered via a pusher, and a severing or degrading system is typically used to sever the coil from the pusher. Thermal, electrolytic, or mechanical detachment means can be used to detach the coil from the pusher. One such thermal detachment system that could be used is shown in U.S. Pat. No. 8,182,506, which is hereby incorporated by reference in their entirety. Another detachment system that could be used is shown in U.S. Pat. No. 6,620,152, which is hereby incorporated by reference in its entirety.

II. Embolic Coil

Figure 15:
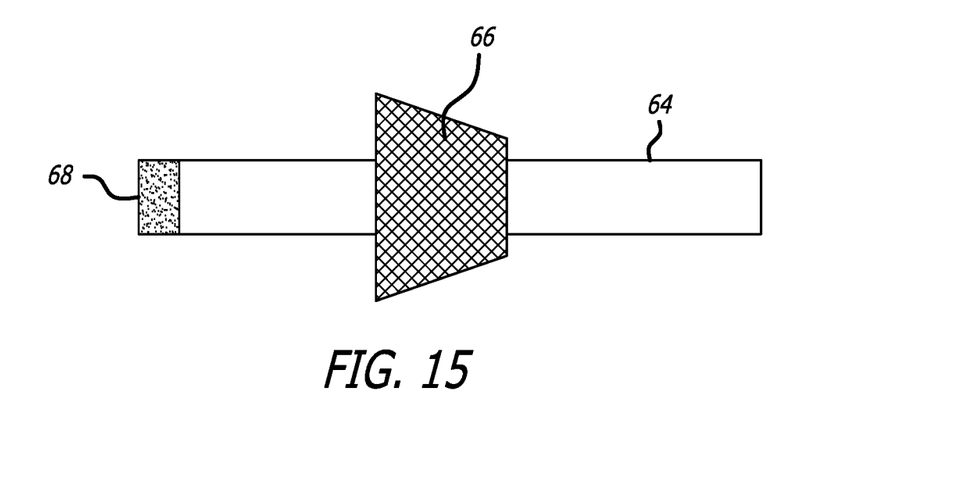
FIG. 15-16 are plan views of an embolic coil as used in an occlusive system in accordance with the present invention.
Figure 16:
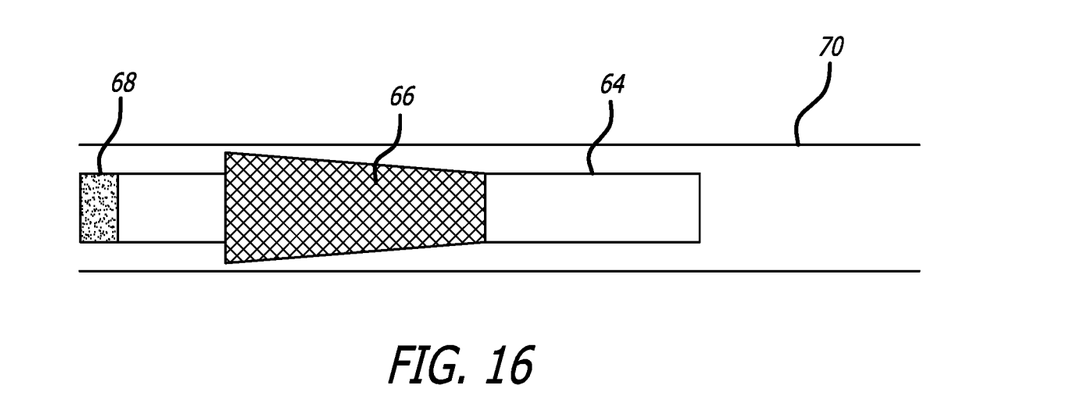

FIGS. 15-16 show an embolic coil that can be used with the occlusive system embodiments shown in FIGS. 1-14. Due to the potential size of the treatment site (e.g., left atrial appendage), as well as the potential for complex geometry, occlusion may be difficult.

FIGS. 15-16 illustrate an embolic coil 64 with a coupler or junction 68 which is connected to the pusher, this junction 68 can be degraded to release the embolic coil 64 at the treatment site. The coil 64 also includes a sheet 66 which is affixed to the coil 64. In one example the sheet 66 is glued or tied on one end to the coil 64 while the other end is free, the sheet 66 can be made of a polymer or can be a metallic mesh. In one example the sheet 66 is a rectangular or round/ovular/elliptical shape with a hole in it and which is placed over the coil 64 and tied, glued, or affixed via other means to the coil.

FIG. 15 shows the coil 64 with the sheet 66 in an expanded position. Multiple sheets 66 can be placed along the length of the embolic coil 64 and the addition of the sheets 66 increases the space filling potential of the coil 64 since one end of the sheet is open and thus free to fill open space within the treatment region. The sheet(s) 66 will also provide a fixation point for the coils 64 where the sheets 66 may contact the vessel wall thus promoting coil stability within the target region.

FIG. 16 shows the embolic coil 64 with the attached sheet 66 in a delivery configuration within a catheter 70. The embolic coil 64 described may also be used to occlude an aneurysm, atrial septal defect, patent foramen ovale, etc.

In one embodiment sheet 66 is a polymer, in another embodiment it is a braided metallic mesh, in another embodiment the sheet is a combination of a polymer and metallic mesh. In another embodiment the sheet(s) 66 are not affixed to the coil and are mobile along the length of the coil. In another embodiment the sheet(s) are not affixed to the coil at all and can be used independently (i.e. loading the sheets in lieu of using embolic coils, using the sheets first then following with coil occlusion).

It will be appreciated by one of ordinary skill in the art that the embodiments of FIGS. 1-16 can be used interchangeably. For example, the embodiments of FIGS. 1-5 could be used with the embodiments of FIGS. 6-12 by integrating the plunger/bag near the distal end of the inner catheter which runs through the mesh. Similarly, this concept could be incorporated on the embodiments of FIGS. 13-14.

III. Vascular Plug

Figure 17:
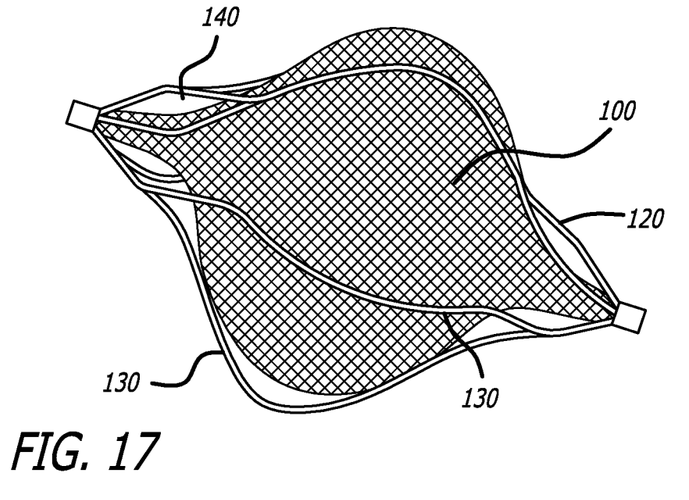
FIGS. 17-19 illustrate an occluder with an inner and outer structure in accordance with the present invention.

One embodiment of a vascular plug in accordance with the present invention is shown in FIG. 17. The plug comprises an inner layer 100 and outer layer 120. The outer layer 120, which may be fabricated from a hypotube, acts as a frame or scaffold, and contacts the vessel wall in one or more locations to prevent the plug from migrating. The outer layer 120 may be metallic and comprised of nitinol, stainless steel, cobalt-chromium, various combinations thereof, or other materials. In one example, outer layer 120 is a laser cut nitinol hypotube.

The inner layer 100 comprises a mesh which can be heat set into particular shape (e.g., spherical). The inner layer 100 may be metallic and comprised of nitinol, stainless steel, cobalt-chromium, various combinations thereof, or other materials. The wires comprising inner layer 100 preferably have minimal gap to limit the amount of blood flow through the plug so as to promote occlusion of the treatment site. In one example inner layer 100 is a 144 wire braid with about a 96 micron pore size and 0.001" OD wire.

Figure 20:
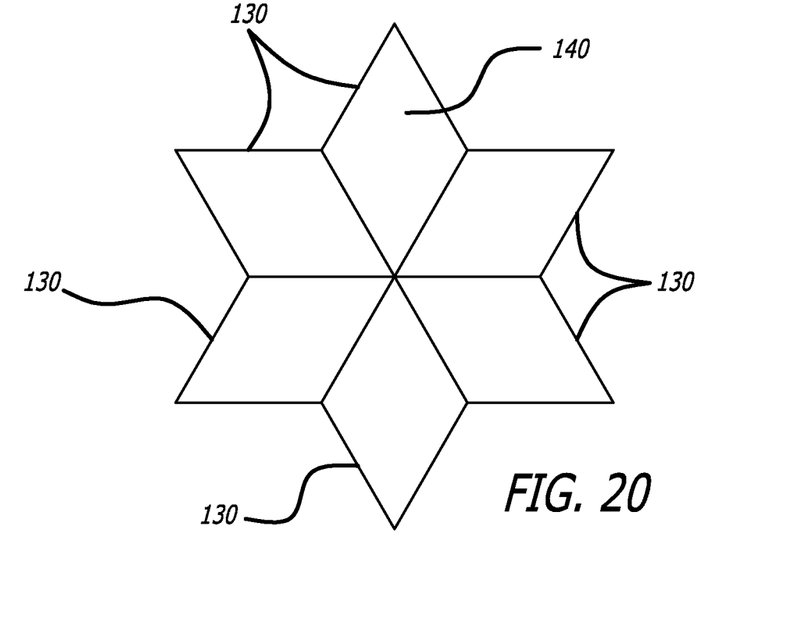
FIG. 20 illustrates the outer structure strut pattern of FIG. 17 in accordance with the present invention.

In one example, outer layer 120 is comprised of 5-10 struts 130. In another example outer layer 120 is comprised of 6 struts 130 and has an elongated spherical shape. When viewed along an axis of the plug (i.e., when viewing either end of the plug along the plug axis), the proximal and distal ends of the outer layer 120 take on a star-like shape comprised of one or more cells 140 as shown in FIG. 20. The star shaped pattern shown in FIG. 20 is based on a 6 strut pattern in which each cell 140 considered to constitute one strut 130. The struts 130 then merge out into a more expanded, elongated spherical frame shape as shown in FIG. 17.

Figure 18:
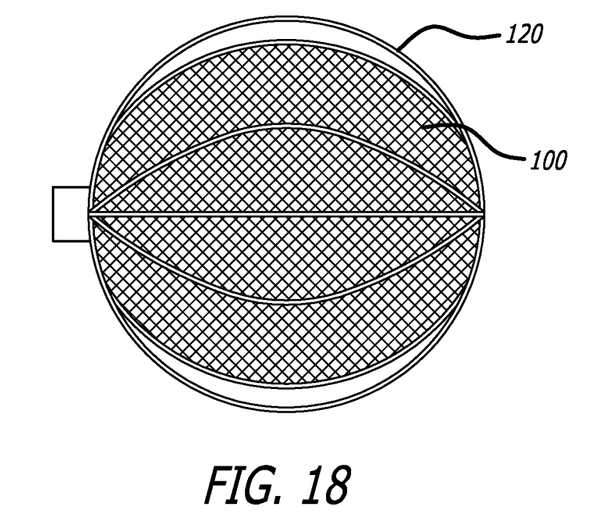
Figure 19:
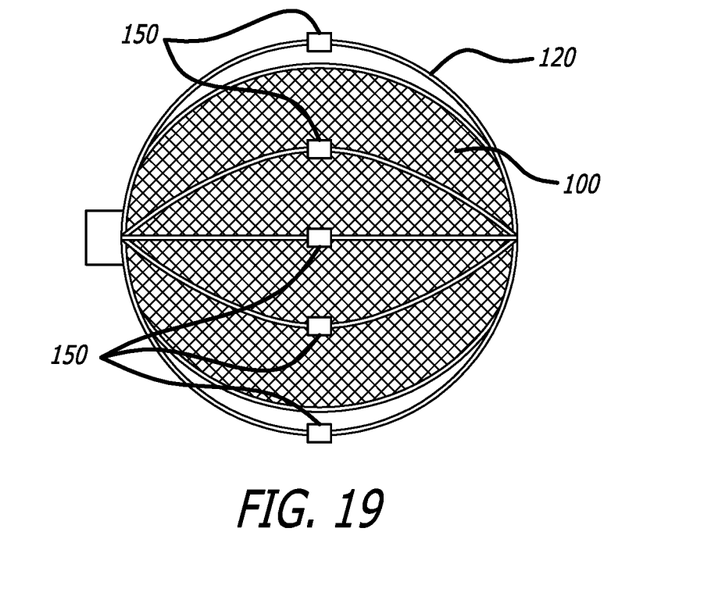

FIGS. 18-19 illustrate a vascular plug with an inner layer 100 and outer layer 120 where the outer layer 120 has a more spherical shape and which conforms more closely to the shape of the inner layer 100 as compared to the shape of outer layer 120 of FIG. 17. In one example of FIG. 18, this more spherically shaped outer layer would not have a star like strut at each end (as in FIG. 20) when viewed along the plug's axis.

Inner layer 100 may utilize radiopaque (i.e. tantalum, platinum, or gold) wires as part of the mesh to promote visualization within the vasculature. In another example shown in FIG. 19, radiopaque markers 150 may be used in select locations along outer layer 120 to enhance visualization. Markers 150 may also be used on the device of FIG. 17.

Figure 21:
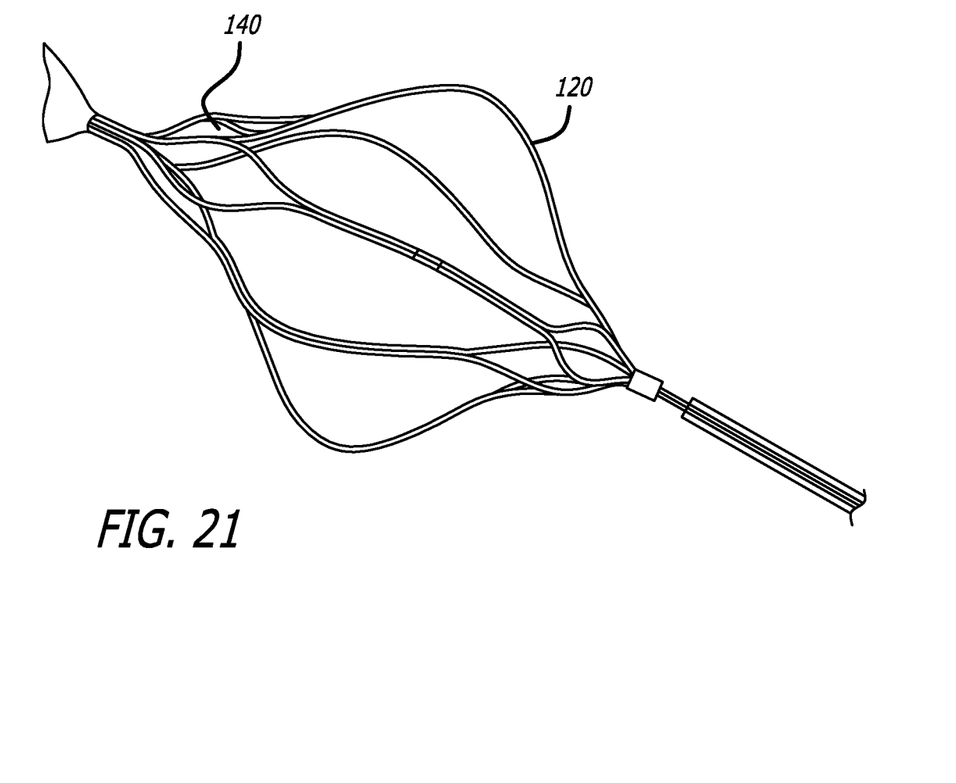
FIGS. 21-22 illustrate an occluder with an inner structure and outer membrane layer in accordance with the present invention.
Figure 22:
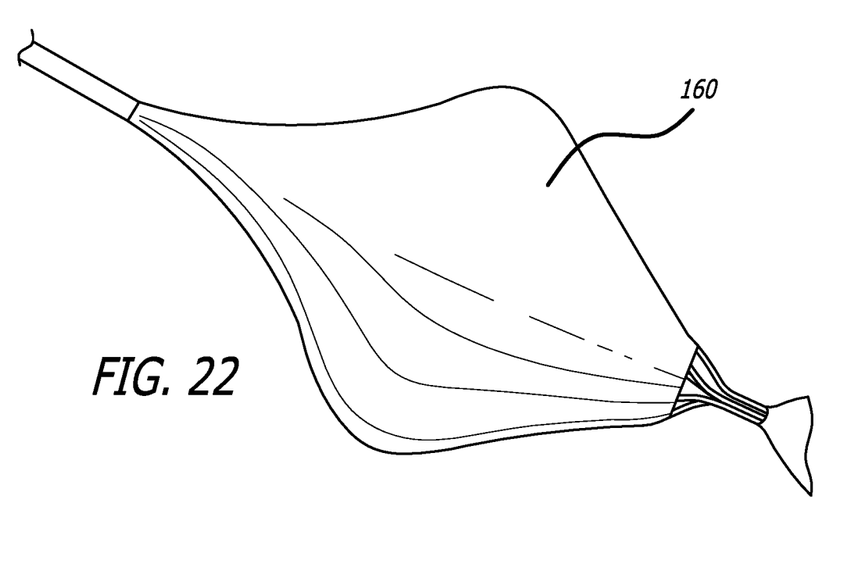

FIGS. 21-22 show another embodiment of a vascular plug in accordance with the present invention. This embodiment contains an inner structure which can be considered analogous to the outer layer 120 of the embodiment of FIG. 17. Instead of an inner layer 100, this embodiment utilizes a membrane 160 over a support structure 120. In one example the membrane 160 may be fixed to support structure 120. In another example, the membrane 16 may be heat set over support structure 120. In another example, adhesive may be used to bond membrane 160 to support structure 120. In one example, the membrane 160 is comprised of a polymer. In one example, that polymer may be ePTFE. In another example, polyester, polyurethane, or PLGA may be used. Radiopaque markers 150 similar to the ones shown in FIG. 19 may be mounted on support structure 120 to promote visualization. Similar to the inner layer 100 of the embodiment of FIG. 17, the membrane 160 substantially prevents blood flow in the vessel and promotes occlusion.

Figure 23:
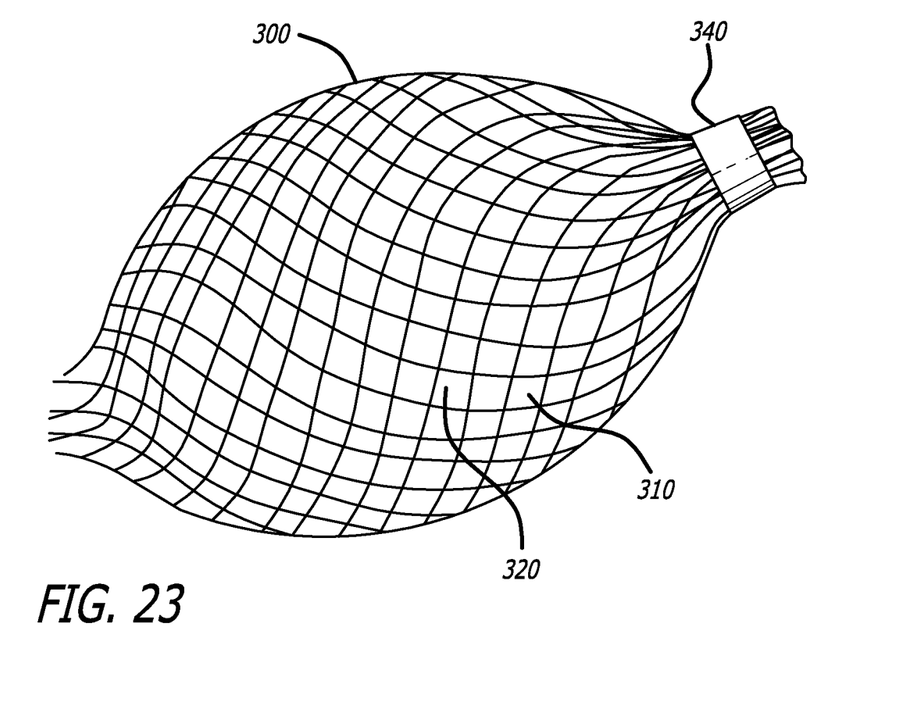
FIG. 23 illustrates an occluder with an inner and outer structure and intermediate membrane layer in accordance with the present invention.

FIG. 23 shows another embodiment of a vascular plug in accordance with the present invention. This embodiment utilizes an outer structure 300, inner structure 310 (not visible in FIG. 23) and a membrane 320 sandwiched between the two structures. In one example, the inner and outer structures 300, 310 are spherical in shape and comprised of a mesh or braid. The proximal and distal ends of the braid layers may be crimped together with radiopaque markers 340. In one example, the markers 340 are stainless steel coated with tantalum. The markers 340 both tie the ends of the braid and allow the device to be visualized within the vasculature during deployment.

In one example, the distal marker crimp utilizes one marker for the inner structure 310 and a separate marker for the outer structure 300 and thus enables the two structures to expand independently from each other. In other words, such a configuration would allow the outer structure 300 to open before the inner structure 310 opens. The extent that each structure opens would depend on the heat set memory of each structure.

The plug is delivered in a collapsed state and expands upon deployment once deployed from the catheter and allows for a variable diffusive blood flow profile depending on the extent that the inner braid is opened. In other words, if the inner structure 310 is not fully opened, the pore size is smaller than if the inner structure 310 is in a fully opened state thus the plug would be more occlusive in nature in such a configuration. As such, in certain embodiments, the inner and outer structures 310, 300 are independently and controllably expandable relative to one another.

The membrane 320 may be comprised of a polymer. In one example, that polymer is ePTFE. In another example, polyester, polyurethane, or PLGA may be used. The inner structure 310 provides a foundation layer for the membrane 320, while the outer structure 300 provides increased restraining force to the membrane 320 while also providing another barrier for blood flow. In one example, the membrane 320 may be adhesively bonded, heat set, or tied to either the inner or outer structure, 310, 300 or both structures. In one example the inner and outer structures, 310, 300 are made with 48 wires, 0.0019" diameter wire. In one example radiopaque wires (i.e. tantalum) are weaved into the braid to provide radiopacity. The structures 310, 300 may be heat set into the desired shape (e.g., spherical).

In another embodiment similar to the embodiment of FIG. 23, no inner structure is used and the membrane 320 is affixed only to the outer structure 300. Such fixation can be achieved through an adhesive, mechanically or by a heat set operation, etc.

Figure 24:
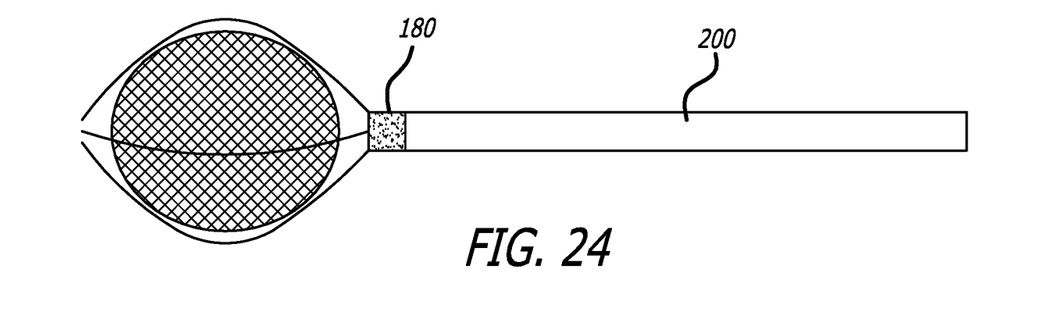
FIG. 24 illustrates a delivery system for an occluder in accordance with the present invention

FIG. 24 illustrates a delivery system used to deliver an occlusive plug in accordance with the present invention. The delivery system comprises a pusher 200 and a linkage 180. The linkage 180 is degradable to sever the plug from the pusher 200. In one example, pusher 200 is a push wire. In another example pusher 200 is a hypotube. Mechanical (e.g., screw threads), hydraulic, thermolytic, or electrolytic systems may be used to degrade linkage 180. One such detachment system that could be used is shown in U.S. Pat. No. 8,182,506, which is hereby incorporated by reference in its entirety. Another detachment system that could be used is shown in U.S. Pat. No. 6,620,152, which is also hereby incorporated by reference in its entirety. The device could be delivered through a catheter and is detached at the target site.

In one embodiment, the plug is collapsible and is delivered in a contracted shape in the catheter and adopts its enlarged deployed shape once deployed from the catheter. In another embodiment the plug is delivered through a catheter which is large enough to accommodate the plug in its deployed shape. As such, the plug is delivered and deployed in its final shape.

For any embodiment utilizing a membrane, the pore size of the membrane may be customized depending on the desired occlusion rate. A smaller pore size will generally occlude blood flow quicker than a larger pore size membrane. Thus if rapid occlusion is desired, a smaller pore size membrane is used and if slower occlusion is desired a larger pore size membrane is used. Alternatively, only a portion of the structure is covered with the membrane, e.g., a third or a half of the support structure is covered with the membrane, which will cause occlusion to take longer than if the complete structure is covered with the membrane.

Similarly, for any embodiments utilizing inner layer 100, the pore size of the inner layer 100 may be customized depending on the desired occlusion rate. A smaller pore size for the inner layer 100 is used when rapid occlusion is desirable, and a larger pore size for the inner layer 100 is used when slower occlusion is desirable.

For any of the above-described embodiments employing an inner layer or structure 100 and an outer layer or structure 120, the proximal and distal ends of the layers may be crimped together with radiopaque or non-radiopaque markers. In one example, the radiopaque markers are stainless steel coated with tantalum. Such markers serve to tie or bind the ends of the layers and, if radiopaque, allow the device to be visualized within the vasculature during deployment. The proximal ends of the inner layer or structure 100 and proximal ends of the outer layer or structure 120 may be crimped together or independently of one another. Likewise, the distal ends of the inner layer or structure 100 and proximal ends of the outer layer or structure 120 may be crimped together or independently of one another. Embodiments in which the ends of the inner layer or structure 100 and the outer layer or structure 120 are independently crimped allow for the inner layer or structure 10 and the outer layer or structure 120 to expand independent of one another. Accordingly, a variable diffusive blood flow profile is achieved depending upon the extent that the layers or structures are opened. For example, if the inner layer is not fully opened, the pore size would be smaller than the pore size when inner layer is in the fully opened state and thus more occlusive in nature). In other words, in certain embodiments, the inner and outer structures are independently and controllably expandable relative to one another.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vascular occlusion device to occlude a treatment site comprising:
   an outer tube;
   an inner tube positioned within and extending beyond the outer tube;
   a vascular plug attached distally to the inner tube and proximally to the outer tube, the vascular plug comprising an inner layer and an outer layer, wherein the inner layer comprises a mesh, and wherein the outer layer comprises a plurality of struts;
   a hemostatic valve connected to the outer tube; and
   a fitting connected adjacent to the hemostatic valve, the fitting being adjustable between a first configuration in which the fitting locks the inner tube relative to the outer tube to thereby fix a radial shape of the vascular plug and a second configuration in which the fitting does not lock the inner tube relative to the outer tube;
   an introducer located at and in fluid communication with a proximal end of the inner tube; and,
   where the inner tube can be pushed or pulled independently of the outer tube to control a radial shape of the vascular plug.

2. The vascular occlusion device of claim 1, further comprising a first fitting connecting the outer tube to the hemostatic valve.

3. The vascular occlusion device of claim 2, wherein the hemostatic valve includes a second fitting threadably connected to the first fitting.

4. The vascular occlusion device of claim 1, where the inner tube contains a lumen used to convey embolic material.

5. The vascular occlusion device of claim 4, wherein the introducer is attached to the proximal end of the inner tube, wherein the introducer is used to place an embolic material through the inner tube.

6. The vascular occlusion device of claim 1, wherein the treatment site is a left atrial appendage.

7. The vascular occlusion device of claim 1, wherein the fitting and the hemostatic valve are each independently operable.

8. The vascular occlusion device of claim 7, wherein the fitting is axially offset with respect to the hemostatic valve.

9. The vascular occlusion device of claim 1, wherein the fitting is threadably engaged with the hemostatic valve.

10. The vascular occlusion device of claim 1, wherein the fitting is rotatable between the first configuration and the second configuration.

11. A vascular occlusion system to occlude a treatment site comprising:
an outer tube;
an inner tube positioned within and extending beyond the outer tube, the inner tube having a lumen allowing passage of material through the inner tube and into the treatment site;
a vascular plug attached distally to the inner tube and proximally to the outer tube, the vascular plug comprising an inner layer and an outer layer, wherein the inner layer comprises a mesh, wherein the outer layer comprises a plurality of struts, and wherein the vascular plug comprises a star-like shape comprising one or more cells when viewed from a proximal end or a distal end of the vascular plug;
a hemostatic valve connected to the outer tube;
where the inner tube can be pushed or pulled independently of the outer tube to radially expand the vascular plug;
a locking mechanism connected adjacent to the hemostatic valve, the locking mechanism being adjustable between a first configuration in which the locking mechanism locks the inner tube relative to the outer tube to thereby fix a radial shape of the vascular plug and a second configuration in which the locking mechanism does not lock the inner tube relative to the outer tube; and, an introducer located at and in fluid communication with a proximal end of the inner tube.

12. The vascular occlusion system of claim 11, wherein the hemostatic valve is attached to a proximal end of the outer tube.

13. The vascular occlusion system of claim 12, further comprising a first fitting connecting the outer tube to the hemostatic valve.

14. The vascular occlusion system of claim 13, wherein the hemostatic valve includes a second fitting threadably connected to the first fitting.

15. The vascular occlusion system of claim 14, wherein the locking mechanism comprises a third fitting connected to a proximal end of the hemostatic valve.

16. The vascular occlusion system of claim 11, further comprising an introducer attached to a proximal end of the inner tube, wherein the introducer is used to place an embolic substance through the inner tube to thereby occlude the treatment site.

17. The vascular occlusion system of claim 11, wherein the treatment site is a left atrial appendage.

18. The vascular occlusion system of claim 11, wherein the locking mechanism and the hemostatic valve are independently operable.

19. The vascular occlusion system of claim 18, wherein the locking mechanism is axially offset with respect to the hemostatic valve.

20. The vascular occlusion system of claim 11, wherein the locking mechanism is threadably engaged with the hemostatic valve.

* * * * *